United States Patent
Suzuki et al.

(10) Patent No.: US 7,189,708 B2
(45) Date of Patent: *Mar. 13, 2007

(54) TOPICAL COMPOSITION FOR SKIN

(75) Inventors: Yasuto Suzuki, Haga-gun (JP); Mikako Watanabe, Haga-gun (JP); Naoko Tsuji, Haga-gun (JP); Shigeru Moriwaki, Haga-gun (JP); Shinya Amano, Haga-gun (JP)

(73) Assignee: Kao Corporation, Tokyo (JP)

( * ) Notice: Subject to any disclaimer, the term of this patent is extended or adjusted under 35 U.S.C. 154(b) by 405 days.

This patent is subject to a terminal disclaimer.

(21) Appl. No.: 10/252,057

(22) Filed: Sep. 23, 2002

(65) Prior Publication Data

US 2003/0087833 A1    May 8, 2003

Related U.S. Application Data

(63) Continuation of application No. 09/678,615, filed on Oct. 4, 2000, now Pat. No. 6,489,291.

(30) Foreign Application Priority Data

Oct. 5, 1999    (JP)    ............................. 11-283794

(51) Int. Cl.
*A61K 31/545*    (2006.01)
(52) U.S. Cl. ............................ 514/200; 514/2; 514/12; 424/642; 424/691
(58) Field of Classification Search ................ 514/19, 514/7, 11, 200; 424/642, 692
See application file for complete search history.

(56) References Cited

U.S. PATENT DOCUMENTS

| | | | | |
|---|---|---|---|---|
| 4,513,009 | A * | 4/1985 | Roques et al. | 514/513 |
| 5,091,171 | A * | 2/1992 | Yu et al. | 424/642 |
| 6,075,052 | A | 6/2000 | Suzuki et al. | |
| 6,171,595 | B1 | 1/2001 | Suzuki et al. | |

FOREIGN PATENT DOCUMENTS

| | | |
|---|---|---|
| EP | 0 054 862 | 6/1982 |
| JP | 2000-119144 | 4/2000 |

OTHER PUBLICATIONS

Mumford, et al., Inhibition of Porcine Kidney "Enkephalinase" by Substituted-N-Carboxymethyl Dipeptides, Biochemical and Biophysical Research Communications, 1982, vol. 109, No. 4, pp. 1303-1309.*

Mumford, et al., Inhibition of Porcine Kidney "Enkephalinase" by Substituted-N-Carboxymethyl Dipeptides, Biochemical and Biophysical Research Communications, 1982, vol. 109, No. 4, pp. 1303-1309.*

Chemical Abstracts, vol. 98, No. 3, Jan. 17, 1983, Abstract No. 11055w.

Patent Abstracts of Japan, vol. 1997, No. 04, Apr. 30, 1997 & JP 08 333230 A (Kao Corp), Dec. 17, 1996, Abstract.

JP Abstract 406345797, Dec. 20, 1994.

* cited by examiner

*Primary Examiner*—Sreenivasan Padmanabhan
*Assistant Examiner*—Leonard Williams
(74) *Attorney, Agent, or Firm*—Oblon, Spivak, McClelland, Maier & Neustadt, P.C.

(57) ABSTRACT

A topical skin composition containing a dipeptide compound represented by formula (1) or a salt of the dipeptide:

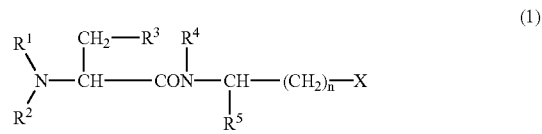

(1)

wherein $R^1$ represents a hydrogen atom, an alkyl group, an alkanoyl group, or —$CH(R^6)COOR^7$ (wherein $R^6$ represents a hydrogen atom or a lower alkyl group, and $R^7$ represents a hydrogen atom, a lower alkyl group, a lower alkenyl group, or an aralkyl group);

$R^2$ represents a hydrogen atom or an alkyl group which may have a substituent;

$R^3$ represents a lower alkyl group or a phenyl group;

$R^4$ represents a hydrogen atom or a lower alkyl group, and may form a heterocyclic ring together with $R^5$ and an adjacent nitrogen atom;

$R^5$ represents a hydrogen atom, an alkyl group which may have a substituent, or an aralkyl group which may have a substituent, and may form the heterocyclic ring together with $R^4$;

X represents —$COOR^8$ (wherein $R^8$ represents a hydrogen atom, a lower alkyl group, a lower alkenyl group, or an aralkyl group) or —$SO_3H$; and n is an integer of 0-4; and a pharmaceutically acceptable carrier therefor.

5 Claims, No Drawings

TOPICAL COMPOSITION FOR SKIN

BACKGROUND OF THE INVENTION

1. Field of the Invention

The present invention relates to a topical composition for the skin (hereinafter may be simply referred to as a topical skin composition) exhibiting effects of retarding aging of the skin or rejuvenating the skin and of suppressing hair growth.

2. Background Art

Studies have revealed that aging of the skin is mainly caused by advancing age, drying, oxidation, or sunlight (i.e., UV rays). Aging of the skin is recognized by a decrease in collagen or elastin in the dermis of the skin; a decrease in mucopolysaccharides, including hyaluronic acid; or the presence of cells which are damaged by UV rays.

For the prevention of wrinkle formation, however, sufficient effects have not yet been attained, for example, by a collagen-containing cosmetic composition. In addition, a number of research projects have focused on skin aging caused by exposure to UV rays. However, cosmetic compositions superseding UV absorbing agents or UV protecting agents have not yet been developed.

There is a trend towards a preference for hairless bodies, particularly, hairless arms or legs, for reasons of aesthetic appearance. Various methods have been tried in the pursuit of body hair removal, for example, a mechanical hair-removal method making use of a shaver or hair-tweezers, a method for removing body hair from the hair root by use of a hair removing agent, and a method for removing body hair through chemical action of a hair removing agent.

However, the aforementioned hair removing methods physically or chemically stimulate the skin, and are limited by the unsatisfactory duration of the hairless state. Therefore, there is a need for the development of a method which facilitates removal of body hair.

SUMMARY OF THE INVENTION

In view of the foregoing, an object of the present invention is to provide a topical composition for the skin exhibiting effects with respect to retarding aging of the skin, such as wrinkle formation, or rejuvenating the skin, and of suppressing hair growth.

The present inventors have found that a dipeptide compound having a specific structure or a salt thereof exhibits excellent effects with respect to suppressing wrinkle formation, preventing a reduction in skin elasticity, and suppressing hair growth, and that the compound or the salt is effectively employed in a topical skin composition for retarding aging of the skin or suppressing hair growth.

Accordingly, the present invention provides a topical skin composition comprising a dipeptide compound represented by formula (1) or a salt of the dipeptide:

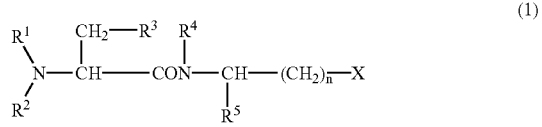

(1)

wherein $R^1$ represents a hydrogen atom, an alkyl-group, an alkanoyl group, or —CH($R^6$)COOR$^7$ (wherein $R^6$ represents a hydrogen atom or a lower alkyl group, and $R^7$ represents a hydrogen atom, a lower alkyl group, a lower alkenyl group, or an aralkyl group);

$R^2$ represents a hydrogen atom or an alkyl group which may have a substituent;

$R^3$ represents a lower alkyl group or a phenyl group;

$R^4$ represents a hydrogen atom or a lower alkyl group, and may form a heterocyclic ring together with $R^5$ and an adjacent nitrogen atom;

$R^5$ represents a hydrogen atom, an alkyl group which may have a substituent, or an aralkyl group which may have a substituent, and may form the heterocyclic ring together with $R^4$;

X represents —COOR$^8$ (wherein $R^8$ represents a hydrogen atom, a lower alkyl group, a lower alkenyl group, or an aralkyl group) or —SO$_3$H; and n is an integer of 0–4; and a pharmaceutically acceptable carrier therefor.

The present invention also provides, as a novel compound which has not yet been described in any literature, N-(carboxymethyl)phenylalanyl-β-alanine, among dipeptide compounds represented by formula (1), or a salt thereof.

Various other objects, features and many of the attendant advantages of the present invention will be readily appreciated as the same becomes better understood by reference to the following detailed description of the preferred embodiments.

DETAILED DESCRIPTION OF PREFERRED EMBODIMENTS

In formula (1), an alkyl group represented by $R^1$ is preferably a C1–C6 alkyl group, may be a linear or branched alkyl group, and is more preferably a methyl group, an ethyl group, an n-propyl group, an isopropyl group, an n-butyl group, an isobutyl group, or a t-butyl group.

An alkanoyl group represented by $R^1$ is preferably a C1–C6 alkanoyl group, may be a linear or branched alkanoyl group, and is more preferably an acetyl group, a propionyl group, or a butyryl group.

A lower alkyl group represented by $R^3$, $R^4$, $R^6$, $R^7$, or $R^8$ is preferably a C1–C6 alkyl group, may be a linear or branched alkyl group, and is more preferably a methyl group, an ethyl group, an n-propyl group, an isopropyl group, an n-butyl group, an isobutyl group, or a t-butyl group.

A lower alkenyl group represented by $R^7$ or $R^8$ is preferably a C2–C6 alkenyl group, more preferably a vinyl group or a propenyl group.

An aralkyl group represented by $R^7$ or $R^8$ is a C7–C18 aralkyl group. Specific examples include a phenyl C1–C6 alkyl group, a biphenyl C1–C6 alkyl group, and a naphthyl C1–C6 alkyl group. Of these, a phenyl C1–C6 alkyl group is preferable, and a benzyl group is more preferable.

An alkyl group which may have a substituent, represented by $R^2$, may be a C1–C6 alkyl group, a carboxy C1–C6 alkyl group, or a C1–C6 alkoxycarbonyl C1–C6 alkyl group. Of these, a C1–C6 alkyl group is preferable. $R^2$ is more preferably a methyl group, an ethyl group, an n-propyl group, an isopropyl group, an isobutyl group, or a t-butyl group.

An alkyl group which may have a substituent, represented by $R^5$, may be a C1–C6 alkyl group, a carboxy C1–C6 alkyl group, or a C1–C6 alkoxycarbonyl C1–C6 alkyl group. Of these, a C1–C6 alkyl group and a carboxy C1–C6 alkyl group are preferable. $R^5$ is more preferably a methyl group, an isopropyl group, an isobutyl group, a t-butyl group, a carboxymethyl group, or a carboxyethyl group.

A heterocyclic ring which is formed by $R^4$ and $R^5$ may be pyrrolidine or piperidine.

An integer n is preferably 0, 1, or 2.

In formula (1), $R^1$ is more preferably a hydrogen atom, a C1–C6 alkyl group, a C1–C6 alkanoyl group, or —CH($R^6$)COO$R^7$ (wherein $R^6$ represents a hydrogen atom or a C1–C6 alkyl group, and $R^7$ represents a hydrogen atom, a C1–C6 alkyl group, a C2–C6 alkenyl group, or a phenyl C1–C6 alkyl group). $R^2$ is more preferably a hydrogen atom or a C1–C6 alkyl group. $R^3$ is more preferably a C1–C6 alkyl group or a phenyl group. $R^4$ is more preferably a hydrogen atom or a C1–C6 alkyl group. $R^5$ is more preferably a hydrogen atom, a C1–C6 alkyl group, a phenyl C1–C6 alkyl group, or a carboxy C1–C6 alkyl group. X is more preferably —COO$R^8$ (wherein $R^8$ represents a hydrogen atom, a C1–C6 alkyl group, a C2–C6 alkenyl group, or a phenyl C1–C6 alkyl group) or —SO$_3$H. An integer n is more preferably 0, 1, or 2.

Examples of salts of a dipeptide compound (1) include alkali metal salts, alkaline earth metal salts, amine salts, amino acid salts, and acid addition salts. Of these, alkali metal salts and amino acid salts are preferable. A dipeptide compound (1) may have optical activity, and its steric configuration may be any of R, S, and a racemic mixture. The compound may also be in the form of a hydrate.

Among dipeptide compounds of formula (1), the more preferred compounds are as follows:

(compound 1)
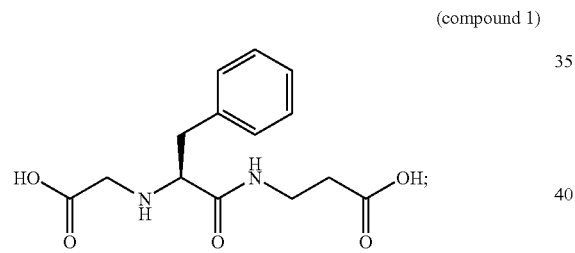

(compound 2)
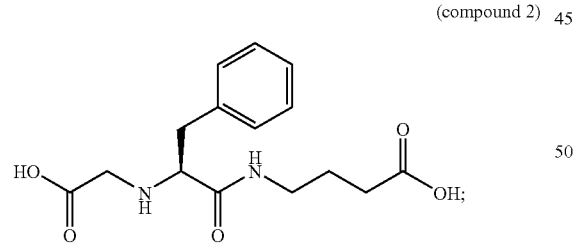

(compound 3)
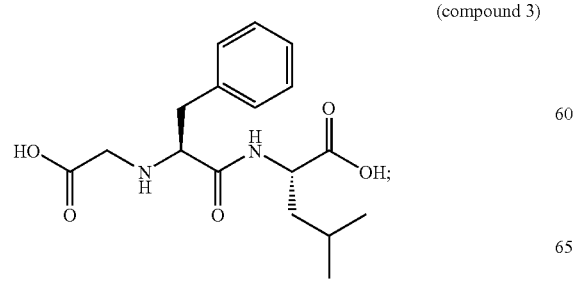

-continued (compound 4)
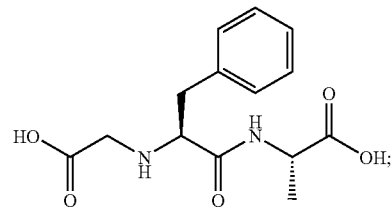

(compound 5)
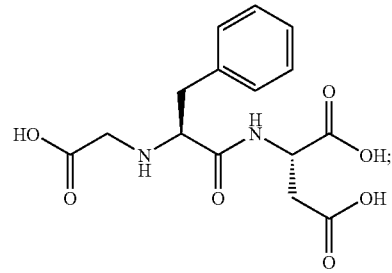

(compound 6)
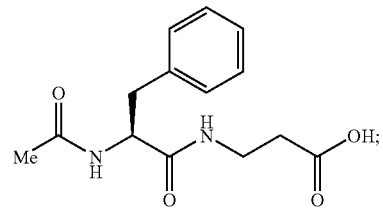

(compound 7)
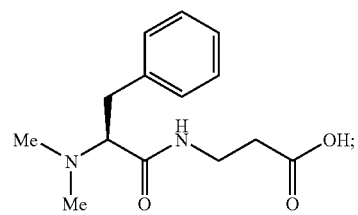

(compound 8)

(compound 9)
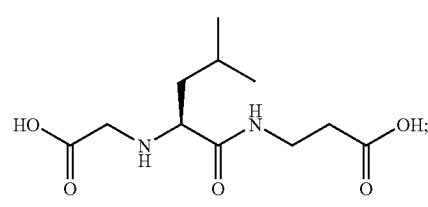

(compound 10)
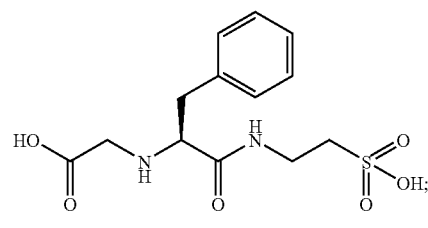

Phe-Gly (compound 11); Phe-β-Ala (compound 12); Phe-Phe (compound 13); Phe-Leu (compound 14); Phe-Ala (compound 15); and Phe-Asp (compound 16): Phe-Tau (compound 17).

Of these, compound 1 and compound 12 are more preferable.

A compound of formula (1) in which $R^1$ is a hydrogen atom may be synthesized through a process described in "K. Ienalga, K. Higashihara, and H. Kimura, Chem. Pharm. Bull., 35, 1249–1254 (1987)." A compound of formula (1) in which $R^1$ is not a hydrogen atom but is any of the aforementioned groups may be synthesized through, for example, the following process:

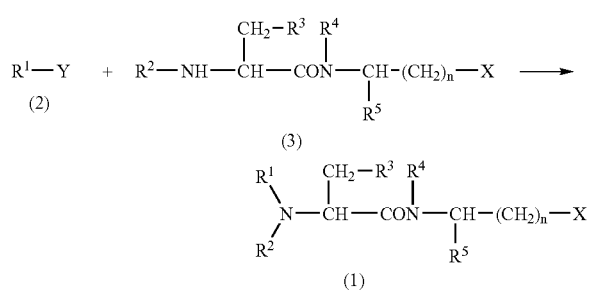

(wherein Y represents a halogen atom, a p-toluenesulfonyl group, or a methanesulfonyloxy group; $R^1$ represents any of the aforementioned groups other than a hydrogen atom; and $R^2$ through $R^5$, n, and X are the same as described above).

Namely, a compound (2) is reacted with a compound (3) in the presence or absence of a base, and if necessary, hydrolysis by use of a base such as sodium hydroxide, or catalytic hydrogenation by use of a catalyst such as palladium carbon may be carried out, to thereby yield a compound (1) of the present invention.

Examples of bases which may be employed in the reaction include sodium hydroxide, potassium hydroxide, potassium carbonate, sodium carbonate, sodium hydrogencarbonate, and triethylamine. Of these, potassium carbonate and triethylamine are preferable, and triethylamine is more preferable.

Examples of solvents which may be employed in the reaction include water, dimethylformamide, tetrahydrofuran, benzene, toluene, xylene, and hexane. Of these, toluene and benzene are preferable, and toluene is more preferable. The reaction temperature is −30 to 200° C., preferably 10 to 90° C., more preferably 40 to 70° C.

A dipeptide compound (1) or a salt thereof is incorporated into the topical skin composition of the present invention in an amount of 0.0001–40 wt. % (hereinafter "wt. %" will be simply referred to as "%"), preferably 0.01–20%.

The topical skin composition of the present invention is more preferably used for preventing and ameliorating unfavorable skin conditions caused by aging of the skin, such as wrinkles, flabbiness, and reduction of elasticity; or for suppressing hair growth.

The topical skin composition of the present invention may further contain a keratinization-ameliorating agent, to thereby enhance the effect of retarding aging of the skin, such as wrinkle formation, or the effect of suppressing hair growth. Examples of such keratinization-ameliorating agents include sphingosine derivatives.

The topical skin composition of the present invention may appropriately contain, in addition to the aforementioned ingredients, a variety of ingredients or carriers which are usually employed in cosmetics, quasidrugs, and drugs. Examples of such ingredients or carriers include humectants, powders, gelation agents, thickeners, surfactants, emulsifiers, anti-inflammatory agents, antioxidants, pH regulating agents, chelating agents, preservatives, dyes, perfumes, UV absorbing agents, UV protecting agents, existing skin-aging preventive or retarding agents such as collagen, and existing hair-growth suppressing agents. The composition may be produced through a conventional method in accordance with the application form.

The topical skin composition of the present invention may be used as a skin composition for pharmaceutical use or a cosmetic composition. Examples of pharmaceutical compositions include a variety of ointments containing a pharmaceutically active ingredient. Such an ointment may comprise an oily base, or an oil-in-water or water-in-oil emulsion base. No particular limitation is imposed on the species of oily base, and, for example, vegetable oil, animal oil, synthetic oil, fatty acid, or natural or synthetic glyceride may be employed. No particular limitation is imposed on the species of pharmaceutically active ingredient, and, for example, analgesic and anti-inflammatory agents, antipruritic drugs, astringent agents, or hormones may be appropriately employed in accordance with needs.

Examples of cosmetic compositions include lotions, emulsions, creams, ointments, sticks, solutions in organic solvents or purified water, packs, gels and aerosols. Namely, the cosmetic composition may be employed as a lotion, an oil essence, an O/W-type or W/O-type cream, a pack, a foundation, a skin-cleansing agent, a tonic, a bathing agent, or an aerosol.

EXAMPLES

Referential Example 1

Phenylalanyl-β-alanine benzyl ester hydrochloride (10.0 g, 0.028 mol) and benzyl bromoacetate (14.6 g, 0.062 mol) were dissolved in tetrahydrofuran (200 mL). To the resultant solution, triethylamine suspended in tetrahydrofuran was added, and the resultant mixture was stirred for 42 hours. After completion of the reaction, the resultant mixture was subjected to extraction with ethyl acetate (100 mL), and the organic layer was washed with a saturated aqueous solution of sodium hydrogencarbonate and saturated brine and then dried over anhydrous sodium sulfate. Subsequently, the solvent was removed, and the resultant residue was subjected to column chromatography with a solvent mixture of ethyl acetate and n-hexane serving as an eluent. Thereafter, the solvent was removed, to thereby obtain a dibenzyl ester (8.8 g, yield: 66%). The ester was suspended in methanol, and then subjected to catalytic hydrogenation by use of palladium carbon (10%). The resultant crystals were subjected to filtration, and then recrystallized from water, to thereby obtain compound 1 (1.34 g, yield: 35%).

NMR (DMSO-$d_6$) δ: 2.30 (t, 2H, J=7 Hz), 2.75 (dd, 1H, J=8, 14 Hz), 2.87 (dd, 1H, J=6, 14 Hz), 3.10 (dd, 2H, J=17, 25 Hz), 3.22 (dt, 2H, J=7, 7 Hz), 3.33 (t, 1H, J=7 Hz), 7.10~7.36 (m, 5H), 7.99 (t, 1H, J=6 Hz)

Referential Example 2

Phenylalanyl-γ-aminobutyric acid methyl ester hydrochloride (1.4 g, 0.0047 mol) and ethyl bromoacetate (0.8 g, 0.0056 mol) were dissolved in tetrahydrofuran (80 mL). To the resultant solution, triethylamine suspended in tetrahydrofuran was added, and the resultant mixture was stirred for 24 hours. After completion of the reaction, the resultant mixture was subjected to extraction with ethyl acetate (20 mL), and the organic layer was washed with a saturated aqueous solution of sodium hydrogencarbonate and saturated brine, and then dried over anhydrous sodium sulfate. Subsequently, the solvent was removed, and the resultant residue was subjected to column chromatography with a solvent mixture of ethyl acetate and n-hexane serving as an eluent. Thereafter, the solvent was removed, to thereby obtain an ethyl ester (0.5 g, yield: 31%). The ester was dissolved in methanol, and an aqueous solution of sodium hydroxide (2.2 equivalent) was added to the methanol solution, and the resultant mixture was stirred for 15 hours. Thereafter, the solvent was removed, and the resultant residue was neutralized with hydrochloric acid. Then the solvent was removed, to thereby obtain compound 2 (0.18 g, yield: 41%).

NMR (DMSO-$d_6$) δ: 1.52 (tt, 2H, J=7, 7 Hz), 2.09 (t, 2H, J=8 Hz), 2.86 (dd, 2H, J=7, 13 Hz), 3.01 (dd, 2H, J=8, 14 Hz), 3.10 (dt, 2H, J=3, 16 Hz), 3.44 (t, 1H, J=7 Hz), 7.04~7.49 (m, 5H), 8.15 (t, 1H, J=16 Hz)

Referential Example 3

The procedure of Referential Example 2 was repeated, except that phenylalanyl-γ-aminobutyric acid methyl ester hydrochloride was replaced by phenylalanyl-leucine methyl ester hydrochloride (1.0 g, 0.00304 mol) and that the amount of ethyl bromoacetate was changed to 0.6 g (0.00365 mol), to thereby obtain compound 3 (0.34 g, yield: 33%).

NMR (DMSO-$d_6$) δ: 0.81 (d, 3H, J=6 Hz), 0.86 (d, 3H, J=6 Hz), 1.40~1.68 (m, 3H), 2.76 (dd, 1H, J=8, 14 Hz), 2.93 (dd, 1H, J=6, 14 Hz), 3.08 (d, 1H, J=17 Hz), 3.23 (d, 1H, J=17 Hz), 3.42 (dd, 1H, J=6, 8 Hz), 4.16~4.28 (m, 1H), 7.17~7.29 (m, 5H), 8.12 (d, 1H, J=8 Hz)

Referential Example 4

Phenylalanyl-β-alanine ethyl ester (10 g, 0.038 mol) and triethylamine (10.3 g, 0.1 mol) were suspended in toluene (45 g), and the suspension was heated to 60° C. To the resultant suspension, ethyl bromoacetate (9.3 g, 0.057 mol) suspended in toluene (5 g) was added dropwise over 0.5 hours, and then the resultant mixture was stirred for three hours. After completion of reaction, the resultant reaction mixture was subjected to extraction with ethyl acetate (20 g). The organic layer was washed with a 2.5% aqueous solution of citric acid. Subsequently, the solvent was removed, to thereby obtain N-(carboethoxymethyl)phenylalanyl-β-alanine ethyl ester (10.7 g, yield: 80.3%). The compound was dissolved in methanol, and a 48% aqueous solution of sodium hydroxide (6.6 g, 0.08 mol) was added to the methanol solution, and the resultant mixture was stirred for three hours. After completion of reaction, the solvent was removed, and the resultant residue was dissolved in water (20 mL), and then washed with ethyl acetate (10 g). Subsequently, hydrochloric acid was added to the aqueous layer, so as to attain a pH of 3.5. After being cooled, the resultant solution was subjected to filtration, to thereby obtain crude crystals. The crystals were recrystallized from a 20% aqueous solution of isopropyl alcohol, to thereby obtain compound 1 (6.0 g, yield: 67%).

Referential Example 5

The procedure of Referential Example 4 was repeated, except that phenylalanyl-β-alanine ethyl ester was replaced by phenylalanyl-alanine ethyl ester (3.7 g, 0.014 mol) and that the amount of ethyl bromoacetate was changed into 3.5 g (0.021 mol), to thereby obtain compound 4 (1.4 g, yield: 33%).

NMR (DMSO-$d_6$) δ: 1.24 (d, 3H, J=7 Hz), 2.78 (dd, 1H, J=8, 14 Hz), 2.96 (dd, 1H, J=5, 14 Hz), 3.08 (d, 1H, J=17 Hz), 3.24 (d, 1H, J=17 Hz), 2.46(dd, 1H, J=7, 7 Hz), 4.29 (dq, 1H, J=7, 7 Hz), 7.13–7.35 (m, 5H), 8.22 (d, 1H, J=7 Hz), 5.5–8.5 (br. s, 2H)

Referential Example 6

The procedure of Referential Example 4 was repeated, except that phenylalanyl-β-alanine ethyl ester was replaced by phenylalanyl-aspartic acid dimethyl ester (7.4 g, 0.024 mol) and that the amount of ethyl bromoacetate was changed into 6.0 g (0.036 mol), to thereby obtain compound 5 (1.0 g, yield: 12%).

NMR (DMSO-$d_6$) δ: 2.54–2.70 (m, 2H), 2.77 (dd, 1H, J=7, 14 Hz), 2.93 (dd, 1H, J=6, 14 Hz), 3.10 (d, 1H, J=17 Hz), 3.28 (d, 1H, J=17 Hz), 3.44 (dd, 1H, J=6, 7 Hz), 4.45–4.55 (m,1H), 7.19–7.29 (m,5H), 8.28 (d, 1H, J=8 Hz)

Referential Example 7

Phenylalanyl-β-alanine (17.4 g, 0.074 mol) was suspended in pyridine (120 g), and the suspension was cooled to 15° C. Acetic anhydride (30 g) was added dropwise to the resultant suspension over one hour. After completion of addition, the temperature of the resultant mixture was returned to room temperature, and the mixture was stirred for 13 hours, and then the reaction was terminated. The resultant reaction mixture was cooled to 5° C., and ethanol (50 mL) was added to the reaction mixture, and the mixture was stirred for 30 minutes, and then the solvent was removed. The resultant residue was subjected to extraction with ethyl acetate (500 mL), and washed with 5% hydrochloric acid, distilled water, and saturated brine, successively, and then dried over anhydrous sodium sulfate. Subsequently, the solvent was removed, and the resultant residue was subjected to column chromatography with a solvent mixture of chloroform and methanol serving as an eluent. Thereafter, the solvent was removed, to thereby obtain compound 6 (11.5 g, yield: 56%).

NMR (DMSO-$d_6$) δ: 1.74 (s, 3H), 2.30 (dd, 2H, J=7, 7 Hz), 2.70 (dd, 1H, J=10, 14 Hz), 2.91 (dd, 1H, J=5, 14 Hz), 3.12–3.36 (m, 2H), 4.35–4.46 (m, 1H), 7.13–7.28 (m, 5H), 8.02 (t, 1H, J=6 Hz), 8.67 (d, 1H, J=8 Hz), 12.22 (br. s, 1H).

Referential Example 8

Phenylalanyl-β-alanine (1 g, 0.0042 mol) was suspended in water (2 g). To the resultant suspension, palladium carbon (10%) (1 g) and a 36% aqueous solution of formaldehyde (7.1 g, 0.042 mol) were added, and the resultant mixture was stirred in an $H_2$ atmosphere at 10 atm. for 24 hours. After completion of reaction, the solvent was removed. The resultant residue was purified through column chromatography, to thereby obtain compound 7 (12.8 mg, yield: 8.1%).

NMR (DMSO-$d_6$) δ: 1.92–2.32 (m, 2H), 2.81 (s, 6H), 2.89–3.32 (m, 2H), 3.11 (dd, 2H, J=6, 13 Hz), 3.94 (dd, 1H, J=4, 10 Hz), 7.00–7.41 (m, 5H), 8.44 (t, 1 H, J=6 Hz), 11.82–12.52 (br. s, 1H)

Referential Example 9

Phenylalanyl-β-alanine (0.5 g, 0.0021 mol) was suspended in water (5 g). To the resultant suspension, palladium carbon (10%) (0.5 g) and propionaldehyde (0.15 g, 0.027 mol) in methanol (5 g) were added, and the resultant mixture was stirred in a $H_2$ atmosphere for 24 hours. After completion of reaction, the solvent was removed. The resultant residue was recrystallized from methanol, to thereby obtain compound 8 (0.13 g, yield: 22.2%).

NMR (DMSO-$d_6$) δ: 0.75 (t, 3H, J=7 Hz), 1.30 (ddt, 2H, J=7, 7, 14 Hz), 2.12–2.44 (m, 2H), 2.28 (dd, 2H, J=7, 7 Hz), 2.65 (dd, 1H, J=8, 14 Hz), 2.81 (dd, 1H, J=6, 13 Hz), 3.16 (dd, 1H, J=6, 8 Hz), 3.13–3.33 (m, 2H), 7.05–7.35 (m,5H), 7.89 (t,1H, J=6 Hz)

Referential Example 10

The procedure of Referential Example 4 was repeated, except that phenylalanyl-β-alanine ethyl ester was replaced by leucyl-β-alanine ethyl ester (2.0 g, 0.009 mol) and that the amount of ethyl bromoacetate was changed into 2.2 g (0.013 mol), to thereby obtain compound 9 (1.6 g, yield: 45%).

NMR (DMSO-$d_6$) δ: 0.85 (d, 6H, J=7 Hz), 1.37 (dd, 2H, J=7, 6 Hz), 1.48–1.68 (m, 1H), 2.37 (t, 2H, J=7 Hz), 3.02 (d, 1H, J=17 Hz), 3.15 (d, 1H, J=17 Hz), 3.27–3.21 (m, 3H), 8.26 (t, 1H, J=6 Hz)

Referential Example 11

Phenylalanyl taurine (2.5 g, 9.18 mmol) and sodium hydroxide (0.58 g, 0.0144 mol) were dissolved in distilled water (25 g), and the solution was heated to 50° C. To the resultant solution, bromoacetic acid (1.5 g, 0.011 mol) in distilled water (3 g) and an aqueous solution of sodium hydroxide were added dropwise simultaneously over 0.5 hours, so as to attain a pH of 10.5–11.5, and the resultant mixture was stirred for three hours. After completion of reaction, concentrated hydrochloric acid was added to the resultant reaction mixture, so as to attain a pH of 3. Thereafter, the solvent was removed, to thereby obtain an N-(carboethoxymethyl)phenylalanyl taurine inorganic salt mixture (7.15 g). The resultant mixture (1 g) was subjected to ODS-gel column chromatography, to thereby obtain N-(carboethoxymethyl)phenylalanyl taurine (0.15 g). The compound was further treated through fractionation HPLC, to thereby yield compound 10 (48 mg).

NMR (DMSO-$d_6$) δ: 2.35 (dd, 2H, J=7.0, 6.5 Hz), 2.97–3.26 (m, 4H), 3.74 (d, 2H, J=3.3 Hz), 4.01 (t, 1H, J=6.7 Hz), 7.19–7.32 (m, 5H), 8.29 (t, 1H, J=5.5 Hz), 9.41 (bs, 1H)

Test Example 1

Suppression of Wrinkle Formation in Hairless Mouse

The back of each hairless mouse (HR/ICR, 6 weeks old at the start of the test, 5 mice per group) was subjected to a single exposure of UV-B rays at a dose of less than 1 MED using a health light lamp (model: SE20, product of Toshiba Corporation). Immediately after the exposure, an 80% ethanol solution (100 μL) containing a 0.1% test compound was applied to the back. The above procedure was carried out daily for 20 weeks. The radiation energy was measured using a UV-radiometer (model: UVR-305/365D, product of Tokyo Optical). In the control group, only 80% ethanol was applied to the back of each mouse during the test. After the test, wrinkle formation was visually observed, and the degree of wrinkle formation was evaluated against the following ratings (wrinkle index). The results are shown in Table 1.

Wrinkle Index
  0: No wrinkle formation.
  1: A few shallow wrinkles were formed.
  2: A slight amount of wrinkles was formed.
  3: Some wrinkles were formed.
  4: Deep wrinkles were formed.

TABLE 1

| Test Compound | Concentration | Wrinkle Index |
|---|---|---|
| Control | — | 3.06 ± 0.13 |
| Compound 1 | 0.1% | 1.25 ± 0.11 |
| Compound 2 | 0.1% | 2.01 ± 0.14 |
| Compound 3 | 0.1% | 1.82 ± 0.09 |
| Compound 4 | 0.1% | 1.75 ± 0.12 |
| Compound 5 | 0.1% | 2.21 ± 0.14 |
| Compound 6 | 0.1% | 2.57 ± 0.20 |
| Compound 7 | 0.1% | 2.34 ± 0.10 |
| Compound 8 | 0.1% | 2.03 ± 0.09 |
| Compound 9 | 0.1% | 2.11 ± 0.11 |
| Compound 10 | 0.1% | 1.95 ± 0.12 |
| Compound 11 | 1% | 2.82 ± 0.18 |
| Compound 12 | 1% | 1.98 ± 0.20 |
| Compound 13 | 1% | 2.64 ± 0.16 |
| Compound 14 | 1% | 2.82 ± 0.22 |
| Compound 15 | 1% | 2.72 ± 0.16 |
| Compound 16 | 1% | 2.50 ± 0.15 |
| Compound 17 | 1% | 1.99 ± 0.12 |

The results shown in Table 1 reveal that dipeptide compounds of formula (1) exhibit excellent effects with respect to suppressing wrinkle formation and retarding aging of the skin or rejuvenating the skin.

Test Example 2

Maintenance of Skin Elasticity in Rat

Three-week-old SD male rats were classified into three groups (five rats per group): a group of rats to which an 80% ethanol solution containing a test compound was applied to pads of hind limbs; a group of rats to which a solvent (80% ethanol) was applied to the pads; and a group of non-treated rats. Each pad was exposed to UV-B rays (less than 1 MED), and then the test compound-containing solution or the solvent was applied to the pad in an amount of 10 μL. The above procedure was carried out three times a week (every other day of the week days) for six weeks.

Skin elasticity was determined using a cutometer (model: SES575, product of Courage Kazaka) as follows. The skin of the pad was subjected to suction at 500 hPa for three seconds, and then released for three seconds. The displacement over six seconds was measured, to thereby obtain Ue and Uf values. The measurement was repeated five times for each pad.

The linearity of elastic fibers was analyzed according to the method of Imokawa et al. (J. Invest. Dermatol., 105, 254–258(1995)) through image analysis of an SEM micrograph. Specifically, samples for scanning electron microscopy (SEM) were prepared by fixing the pad of a rat with Mercox (product of Dainippon Ink and Chemicals, Inc.) under reflux, followed by digestion with formic acid. From SEM micrographs (×1000) of each of the samples, ten typical micrographs were selected and enlarged copies were made. Each of the enlarged micrographs was divided into 16 uniform regions. From each of the regions, any one of the elastic fibers was selected and traced on a transparent film with a line having a fixed width (width: 8 pixels). When the area surrounded by the line tracing the elastic fiber is called A, and the longitudinal length and lateral length of the minimum rectangle surrounding the trace are called B and C, respectively, the linearity of the elastic fiber is represented by A/(B×C). For example, when the trace of the elastic fiber is linear, the linearity becomes 1. The results are shown in Table 2.

TABLE 2

| Test Compound | Concentration | Ue value | Uf value | Linearity |
|---|---|---|---|---|
| No treatment | — | 0.03294 ± 0.00251* | 0.04833 ± 0.01700* | 0.7345 ± 0.0333* |
| Solvent only | — | 0.02125 ± 0.00875# | 0.03333 ± 0.01111# | 0.5133 ± 0.0600# |
| Compound 1 | 0.1% | 0.03153 ± 0.00523* | 0.04711 ± 0.00213* | 0.7221 ± 0.0299* |
| Compound 3 | 0.1% | 0.02985 ± 0.01021* | 0.04323 ± 0.01722* | 0.7013 ± 0.06551* |
| Compound 4 | 0.1% | 0.03009 ± 0.00274* | 0.04533 ± 0.00971* | 0.7153 ± 0.0329* |
| Compound 5 | 0.1% | 0.02694 ± 0.00157* | 0.04285 ± 0.00271* | 0.6652 ± 0.0239* |
| Compound 6 | 0.1% | 0.02433 ± 0.00921* | 0.03913 ± 0.00924* | 0.6078 ± 0.0195* |
| Compound 7 | 0.1% | 0.02623 ± 0.00874* | 0.0412 ± 0.00258* | 0.6423 ± 0.0433* |
| Compound 8 | 0.1% | 0.02708 ± 0.00119* | 0.0427 ± 0.00657* | 0.6976 ± 0.0422* |
| Compound 9 | 0.1% | 0.02793 ± 0.00697* | 0.04295 ± 0.00836* | 0.6892 ± 0.0157* |
| Compound 10 | 0.1% | 0.02972 ± 0.01034* | 0.04498 ± 0.00637* | 0.7021 ± 0.0454* |
| Compound 12 | 1% | 0.03326 ± 0.01267* | 0.04572 ± 0.01862* | 0.7197 ± 0.0321* |
| Compound 17 | 1% | 0.02894 ± 0.0114* | 0.04369 ± 0.00872* | 0.6913 ± 0.0341* |

*$p < 0.05$ (vs. solvent only)
$p < 0.05$ (vs. no treatment)

The results shown in Table 2 reveal that dipeptide compounds of formula (1) exhibit excellent effects with respect to preventing the lowering of skin elasticity due to UV-B rays and also preventing degradation of the three-dimensional structure of the elastic fibers which cause the lowering, and thus the compounds can maintain skin elasticity.

Test Example 3

Hair Growth Suppression in Mouse

The hair on a portion of the backs (size: 2 cm×4 cm) of groups of six-week-old C3H mice, each group consisting of five mice, was carefully shaved so as not to injure the skin using an electric clipper and electric shaver. To the thus-shaved portion, a sample was applied in an amount of 100 μL twice a day for four weeks. Test compounds were dissolved in a solvent (80% ethanol) to attain the concentrations shown in Table 3, to thereby prepare samples. In the control group, only the solvent was applied to the shaved portion. After three weeks, in order to observe hair regrowth, the shaved portion was photographed at a certain magnification, and the ratio of the area of hair regrowth (i.e., the ratio of the area of hair regrowth to that of the shaved area) was compared with that of the control group using an image analyzer. The hair growth suppression ratio (%) was represented by a relative value when the ratio of the area of the hair regrowth in the control group was taken as 100. The results are shown in Table 3.

TABLE 3

| Test compound | Concentration | Hair-growth suppression ratio |
|---|---|---|
| Compound 1 | 0.1% | 82.4% |
| Compound 2 | 0.1% | 73.3% |
| Compound 3 | 0.1% | 72.3% |
| Compound 4 | 0.1% | 80.5% |
| Compound 5 | 0.1% | 71.0% |
| Compound 6 | 0.1% | 58.3% |
| Compound 7 | 0.1% | 69.6% |
| Compound 8 | 0.1% | 77.8% |
| Compound 9 | 0.1% | 77.1% |
| Compound 10 | 0.1% | 79.2% |
| Compound 11 | 1% | 32.9% |
| Compound 12 | 1% | 90.4% |
| Compound 13 | 1% | 78.5% |
| Compound 14 | 1% | 70.9% |
| Compound 15 | 1% | 68.4% |
| Compound 16 | 1% | 75.2% |
| Compound 17 | 1% | 79.5% |

The results shown in Table 3 reveal that dipeptide compounds of formula (1) exhibit excellent effects with respect to suppressing hair growth.

Formulation Example 1

In accordance with the formulation described below, a cream for retarding aging of the skin was produced through a conventional method. The cream exhibited an excellent effect with respect to retarding aging of the skin.

| | (%) |
|---|---|
| Compound 1 or 12 | 0.2 |
| Stearic acid | 2.0 |
| Cetanol | 4.0 |
| Squalene | 8.0 |
| Vaseline | 5.0 |
| Hydrogenated palm oil | 4.0 |
| Polyoxyethylene sorbitan monostearate (20 E.O.) | 1.4 |
| Oleophilic glycerin monostearate | 2.4 |
| Butyl paraben | 0.1 |
| Glycerin | 3.0 |

-continued

|  | (%) |
|---|---|
| 10.0% Potassium hydroxide | 0.2 |
| Perfume | 0.1 |
| Purified water | Balance |
| Total | 100.0 |

Formulation Example 2

In accordance with the formulation described below, a pack for preventing and retarding aging of the skin was produced through a conventional method. The pack exhibited excellent effects with respect to preventing and retarding aging of the skin.

|  | (%) |
|---|---|
| Compound 3 | 3.0 |
| Polyvinyl alcohol | 20.0 |
| Glycerin | 5.0 |
| Ethanol | 16.0 |
| Perfume | 0.1 |
| Dye | 0.1 |
| Purified water | Balance |
| Total | 100.0 |

Formulation Example 3

In accordance with the formulation described below, a hair growth suppression lotion was produced. Specifically, a solution containing ingredients of A and a solution containing ingredients of B were prepared separately. The solution B was added to the solution A, and the resultant mixture was stirred for homogeneity, to thereby produce a hair growth suppression lotion. The lotion exhibited an excellent effect with respect to suppressing hair growth.

|  |  | (%) |
|---|---|---|
| A. | Polyoxyethylene hydrogenated castor oil | 0.8 |
|  | Ethanol | 30.0 |
| B. | Compound 1 or 12 | 1.0 |
|  | Sodium dodecyl sulfate | 0.12 |
|  | Dodecylmethylamine oxide | 0.18 |
|  | Isopropyl alcohol | 15.0 |
|  | Benzyl alcohol | 12.0 |
|  | Glycerin | 2.0 |
|  | Purified water | Balance |
|  | Total | 100.0 |

Formulation Example 4

In accordance with the formulation described below, a hair growth suppression aerosol was produced. Specifically, ingredients of A were uniformly mixed and charged in a container. The container was then filled with solution B through a conventional method, to thereby produce a hair growth suppression aerosol. The aerosol exhibited an excellent effect with respect to suppressing hair growth.

|  |  | (%) |
|---|---|---|
| A. | Compound 1 | 1.0 |
|  | Cetanol | 1.2 |
|  | Propylene glycol | 4.0 |
|  | Ethanol | 8.0 |
|  | Purified water | Balance |
| B. | Liquefied petroleum gas (propellant) | 4.0 |
|  | Total | 100.0 |

The topical skin composition of the present invention exhibits excellent effects with respect to retarding aging of the skin or rejuvenating the skin and suppressing hair growth.

What is claimed is:

1. A topical skin composition comprising a dipeptide compound selected from the group consisting of:

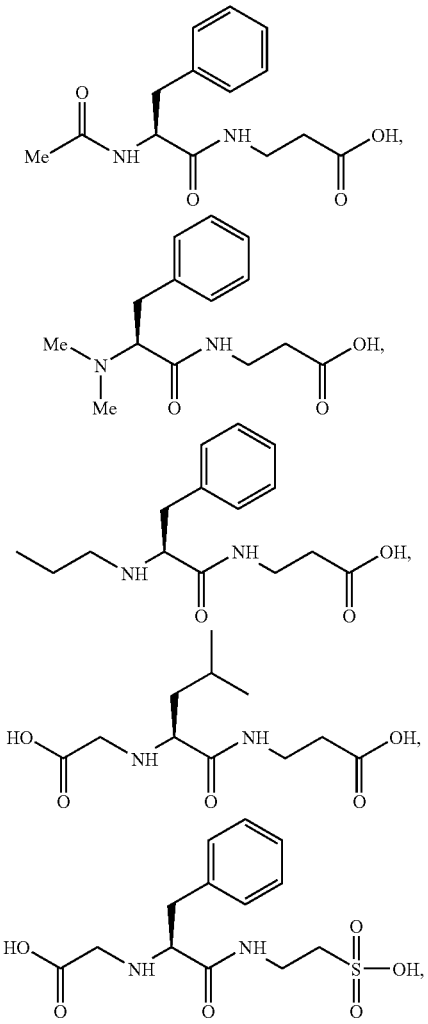

and mixtures thereof;
and a pharmaceutically acceptable carrier therefor.

2. The topical skin composition according to claim 1, wherein said composition is in the form of an ointment.

3. The topical skin composition according to claim 1, wherein said composition is selected from the group consisting of lotions, emulsions, creams, ointment, sticks, solutions in organic solvents, solutions in purified water, packs, gels and aerosols.

4. The topical skin composition of claim 1, wherein said dipeptide compound is present in an amount of 0.0001 to 40 wt. %.

5. The topical skin composition of claim 1, wherein said dipeptide compound is present in an amount of 0.01 to 20 wt. %.

* * * * *